(12) United States Patent
Alterman et al.

(10) Patent No.: US 7,897,257 B2
(45) Date of Patent: Mar. 1, 2011

(54) MAGNETIC BEADS COMPRISING AN OUTER COATING OF HYDROPHILIC POROUS POLYMER AND METHOD OF MAKING THEREOF

(75) Inventors: Mathias Alterman, Uppsala (SE); Andreas Axen, Uppsala (SE); Gunnar Glad, Uppsala (SE); Dag Lindstrom, Vattholma (SE); Ulrika Meyer, Uppsala (SE); Nils Norrman, Uppsala (SE); Tobias Soderman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 391 days.

(21) Appl. No.: 11/911,540

(22) PCT Filed: Apr. 13, 2006

(86) PCT No.: PCT/SE2006/000439
§ 371 (c)(1), (2), (4) Date: Oct. 15, 2007

(87) PCT Pub. No.: WO2006/112771
PCT Pub. Date: Oct. 26, 2006

(65) Prior Publication Data
US 2008/0152939 A1    Jun. 26, 2008

(30) Foreign Application Priority Data
Apr. 18, 2005 (SE) .................................. 0500870

(51) Int. Cl.
B32B 5/16 (2006.01)
B05D 7/00 (2006.01)
(52) U.S. Cl. ...................... 428/407; 427/127; 427/216; 427/221

(58) Field of Classification Search ................. 428/403, 428/407; 427/127, 216, 221
See application file for complete search history.

(56) References Cited

U.S. PATENT DOCUMENTS

| 4,272,510 A | 6/1981 | Smith et al. |
| 4,452,773 A | 6/1984 | Molday |
| 4,582,622 A * | 4/1986 | Ikeda et al. ............... 252/62.53 |

(Continued)

FOREIGN PATENT DOCUMENTS

EP    0 179 039    4/1986

(Continued)

OTHER PUBLICATIONS

Wang, P.-C., et al., "Preparation and Clinical Application of Immunomagnetic Latex", Journal of Polymer Science: Part A: Polymer Chemistry, vol. 43, 1342-1356 (2005).

Primary Examiner—H. (Holly) T Le
(74) Attorney, Agent, or Firm—Yonggang Ji

(57) ABSTRACT

The present invention relates to magnetic beads suitable for, for example, isolation of proteins, cells, and viruses and also for diagnostic applications and cell cultivation. The magnetic beads are composite beads with an inner core of metal particles, which are coated with an inert synthetic polymer and these are then enclosed in a hydrophilic porous polymer, preferably agarose. This provides porous biocompatible beads without metal leakage. The beads may be used for cell cultivation or for chromatography. When the beads are used for chromatography the agarose layer is preferably provided with ligands having affinity for selected biomolecules.

14 Claims, 1 Drawing Sheet

Agarose beads with encapsulated poly(DVB) beads.

U.S. PATENT DOCUMENTS

| | | | |
|---|---|---|---|
| 4,732,811 A * | 3/1988 | Margel | 428/403 |
| 4,783,336 A * | 11/1988 | Margel et al. | 424/462 |
| 4,795,698 A * | 1/1989 | Owen et al. | 435/4 |
| 5,240,640 A * | 8/1993 | Siiman et al. | 516/101 |
| 5,543,289 A | 8/1996 | Miltenyi | |
| 5,776,706 A * | 7/1998 | Siiman et al. | 435/7.21 |
| 5,834,121 A | 11/1998 | Sucholeiki et al. | |
| 5,855,790 A * | 1/1999 | Bradbury et al. | 210/676 |
| 5,858,534 A * | 1/1999 | Sucholeiki | 428/407 |
| 6,013,531 A * | 1/2000 | Wang et al. | 436/526 |
| 6,204,033 B1 | 3/2001 | Muller-Schulte | |
| 6,268,222 B1 * | 7/2001 | Chandler et al. | 436/523 |
| 6,274,387 B1 | 8/2001 | Yamauchi et al. | |
| 6,582,971 B1 * | 6/2003 | Singh et al. | 436/518 |
| 7,108,915 B2 * | 9/2006 | Adams et al. | 428/403 |
| 7,217,457 B2 * | 5/2007 | Elaissari et al. | 428/407 |
| 2009/0092837 A1 * | 4/2009 | Axen et al. | 428/407 |

FOREIGN PATENT DOCUMENTS

| | | |
|---|---|---|
| WO | WO83/03426 | 10/1983 |
| WO | WO/2006/112771 | * 10/2006 |
| WO | WO 2007/114758 A1 * | 10/2007 |

* cited by examiner

Figure 1. poly(DVB)-particles containing magnetic particles.
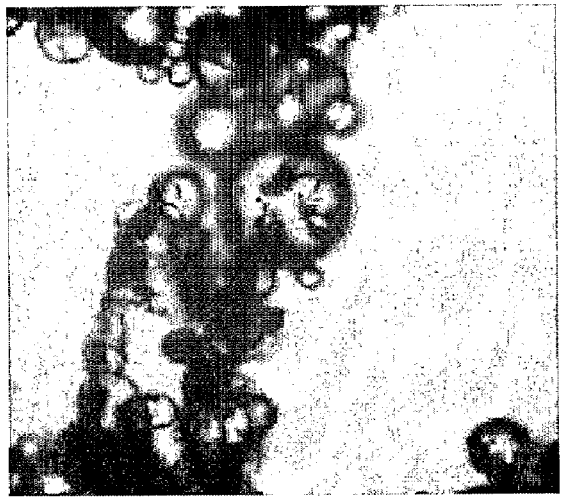
Figure 2. Agarose beads with encapsulated poly(DVB) beads.
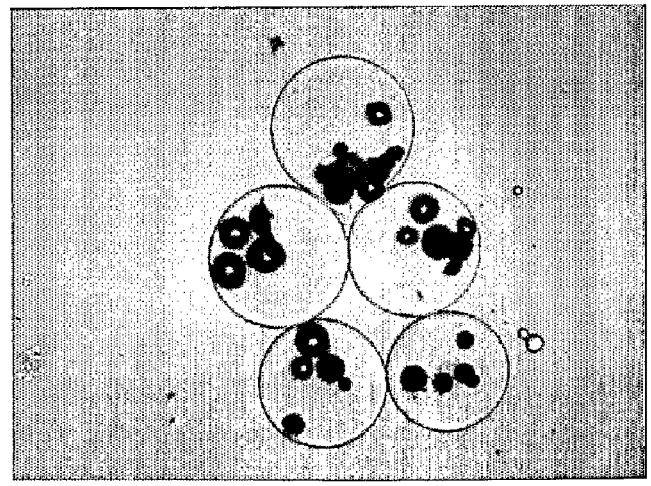

MAGNETIC BEADS COMPRISING AN OUTER COATING OF HYDROPHILIC POROUS POLYMER AND METHOD OF MAKING THEREOF

CROSS-REFERENCE TO RELATED APPLICATIONS

This application is a filing under 35 U.S.C. §371 and claims priority to international patent application number PCT/SE2006/000439 filed Apr. 13, 2006, published on Oct. 26, 2006, as WO 2006/112771, which claims priority to patent application number 0500870-1 filed in Sweden on Apr. 18, 2005; the disclosures of which are incorporated herein by reference in their entireties.

FIELD OF THE INVENTION

The present invention relates to magnetic beads suitable for, for example, isolation of proteins, cells, and viruses and also for diagnostic applications and cell cultivation.

BACKGROUND OF THE INVENTION

Recently an increased number of products referred to as magnetic beads and a number of products for efficient handling of these products have been presented. Magnetic bead technologies are used for diverse purposes such as isolating nucleic acids and proteins as well as viruses and whole cells. The adaptability and speed of this technique makes it ideal for high-throughput applications e.g. in 96 wells micro titre plates. The technique is also applicable for large scale applications, such as chromatography applications in liquid magnetically stabilised fluidised beds.

The magnetic beads are most commonly used in combination with attached ligands having affinity for different substances. The most commonly encountered examples are metal chelating ligands (of IMAC type) intended for use in combination with His-tags and glutathione intended for use in combination with GST (Gluthathione S transferase). Other examples are a variety of different IgG's with different specificity.

Preparation of beads encapsulating metallic materials and applications of magnetic beads has been described previously. Preparing magnetic beads where the bead is built up of different layers of material has also been presented earlier.

U.S. Pat. No. 5,834,121 describes composite magnetic beads. Polymer coated metal oxide particles that are encapsulated in a rigid and solvent stable polymer of vinyl monomers in order to retain the metal oxide particles during harsh conditions. The primary beads are enclosed in a micro porous polymer bead which is capable of swelling in organic solvents and allowing for further functionalisation in order to be useful for organic synthesis. This procedure is aiming for hydrophobic beads.

U.S. Pat. No. 6,204,033 describes preparation of polyvinyl alcohol-based magnetic beads for binding biomolecules. Preparation of magnetic beads by polyvinyl alcohol in water containing magnetic particles. The final beads contain hydroxyl functionalities that can be further derivatized in order to couple biomolecules. It is claimed that these magnetic beads can be grafted with vinyl monomers carrying various functional groups.

U.S. Pat. No. 6,274,387 describes a magnetic carrier, preparation thereof, and a method of extraction of nucleic acid. Particulate silica containing magnetic material is covered with polyacryl amide.

EP 0179039 describes polymer coated metal surfaces. Dextran carrying imino diacetate groups are allowed to attach to a metal surface. Several rounds of activation and coupling of dextran is required to build up a particle. To the dextran various ligands can be attached.

In J. of Polymer Science: Part A: Polymer Chemistry p. 1342-1356, (2005), preparation and clinical application of immunomagnetic latex is described by Wang et al. Magnetic metal oxide particles were encapsulated in poly(methyl methacrylate) [PMMA]. In order to add —COOH functional groups to the surface, a core of poly(methyl methacrylate-co-methacrylic acid) [P(MMA-MAA)] was added.

In spite of the relatively large number of magnetic beads described today, there is still a need of porous beads adapted to large as well as lab scale applications. Especially, there is a need of biocompatible magnetic beads intended for cell separation/cultivation which are free of metal leakage that might have a negative effect on the cells.

SUMMARY OF THE INVENTION

The present invention relates to a novel construction that provides a magnetic beaded material constructed in such a way that low metal leakage is combined with a hydrophilic, biocompatible outer core as carrier for the selected affinity ligand.

According to the present invention magnetic metal oxide particles are coated in an inert synthetic polymer and subsequently the particles are coated with a porous outer layer of agarose. This coating procedure provides magnetic beads with low risk of leakage of metal ions even at harsh conditions, in combination with a hydrophilic, bio compatible outer layer.

Thus, in a first aspect the present invention provides magnetic beads, comprising one or more inner beads of magnetic metal particles enclosed by a coating of an inert synthetic polymer, and an outer coating of a hydrophilic polymer. Preferably the magnetic beads comprise at least two inner beads.

The magnetic beads comprise magnetic metal particles, such as metals, metal oxides or alloys, comprising at least one inner coating of an inert synthetic non-porous polymer layer and an outer coating of a porous layer.

Preferably, the inner coating is made of crosslinked polystyrene, for example poly(divinyl benzene), but other synthetic polymers such as crosslinked poly(methacrylates), polyacrylates or vinyl ethers can be used.

This coating prevents metal leakage from the magnetic metal particles. An additional inner coating of any suitable material preventing metal leakage may also be present, for example as shown in the experimental part.

According to the invention the outer coating is made of a natural or synthetic hydrophilic polymer. Hydrophilic properties are very important for obtaining higher absorption capacity, biocompatibility, and prevention of unspecific interactions.

Preferably, the outer coating is made of agarose. Other examples are carbohydrate polymers, such as dextran and cellulose. Further alternatives of hydrophilic coatings are poly(vinyl alcohol) or polyacrylamides.

The mean particle diameter of the total bead is 5-1000 μm, such as 10-400 μm, or 10-50 μm, depending on the use of the magnetic beads.

In a preferred embodiment the inner coating is made of poly(divinylbenzene) and the outer coating is made of agarose.

Optionally, the outer coating is provided with ligands having affinity for selected biomolecules.

The invention can be used in combination with a large variety of ligands. The ligands may for example be selected from the group consisting of metal chelating agents, antibodies, fractions of antibodies, proteins, members of affinity pairs, aptamers, hybridisation probes, charged groups (suitable for ion exchange) or lipophilic groups (suitable for hydrophobic interaction, HIC).

In a preferred embodiment of the invention, the magnetic metal particles are made of $Fe_3O_4$, the inner coating is made of poly(divinylbenzene), the outer coating is made of agarose.

The pore size of the bead composite is 1 nm-50 µm, preferably 50-500 nm.

In a second aspect, the invention relates to a method of producing magnetic metal particles, comprising the following steps:
a) treating magnetic metal, metal oxide or alloy particles with an amphiphilic agent such as SDS, oleic acid, n-octadecylphosphonic acid or with a silane reagent such as dimethyl dichlorosilanes;
b) adding a polymerisable monomer and a radical initiator to the treated magnetic particles.
c) emulsifying the monomer/particle mixture in an aqueous phase and polymerising the monomer by increasing the temperature to obtain polymer-coated magnetic particles.
d) adding a hydrophilic polymer to the polymer-coated magnetic particles.
e) emulsifying the polymer-coated magnetic particles into the hydrophilic polymer; and optionally
f) attaching a ligand to the outer layer of the hydrophilic polymer, said ligand having affinity for a selected biomolecule.

In the above method it is preferred that, the magnetic metal oxide particles are $Fe_3O_4$, the chemically inert polymer is poly(divinylbenzene), and the hydrophilic polymer is agarose.

In a third aspect, the invention relates to use of the magnetic beads described above for separating, concentrating, cultivating, or analysing a biomolecule or cell. The invention is not restricted to any special kind of biomolecule and may for example be selected from the group consisting of a peptide, protein, carbohydrate, nucleic acid, plasmid, virus or cell.

The invention is not restricted to any special type of cells and may be used for any kind of mammalian cells, stem cells or bacterium.

BRIEF DESCRIPTION OF THE FIGURES

FIG. 1 shows poly(DVB)-particles with encapsulated magnetic beads.

FIG. 2 shows agarose beads with encapsulated beads according to FIG. 1.

DETAILED DESCRIPTION OF THE INVENTION

The present invention provides a magnetic agarose bead with a medium size diameter of 5-1000 µm, having a pore size that offers potential for both fast kinetics and high capacity regarding biomolecule adsorption. This is advantageous as compared to several of the currently existing products for lab scale applications, and also offers the possibility to use the same type of media for large scale applications. In addition to these criteria, the beads are chemically stable with regard to metal leakage.

The present inventors have found that encapsulated magnetic materials can be introduced into hydrophilic, porous materials such as agarose. To avoid the problem of metal leakage the magnetic material is first covered or coated with a chemically stable material. In a preferred embodiment, the magnetic material is encapsulated in small crosslinked polystyrene beads that are used as core particles in the preparation of agarose beads.

This approach results in beads that are chemically stable towards metal leakage and at the same time posses an outer layer that offers a more suitable environment for e.g. protein and cell separations.

EXAMPLES

The following examples are provided for illustrative purposes only, and should not be construed as limiting the scope of the present invention as defined in the appended claims.

1. Materials and Methods

A: Synthesis of Magnetic Poly(Divinyl Benzene) Particles 5 g of iron oxide powder (particle size<5 µm) is added to 50 mL of oleic acid in an Ehrlenmeyer flask. The flask is left on a shaking table at room temperature for an hour. The iron oxide is allowed to sediment, and as much as possible of the oleic acid is removed by decantation.

0.4 g 2,2'-azobis(2-methylbutyronitrile) (AMBN) is dissolved in 20 g divinyl benzene (DVB), tech. 80%, and after complete dissolution of the initiator, the iron oxide particles are added.

A 4% Methocel K-100 (w/v) solution is prepared in advance.

85 g of the methocel solution is added to a 250 mL three-necked round-bottom flask, followed by the organic phase prepared as above. The stirring speed is set at 175 rpm. After 30 minutes the reactor is immersed in an oil bath set at 70 degrees, and the polymerisation reaction is left overnight.

The product particles are sedimented a number of times in water, to remove fines. The particles are then washed on a glass filter with water, 5 M HCl and ethanol. No yellow colour (indicating iron leakage) was observed during the acid wash.

Reducing Particle Size and Using Different Iron Oxides 16 g of iron oxide (9 nm, 20-30 nm or <5 µm) are wetted by 3-6 ml oleic acid.

1.25 g AMBN is dissolved in 62.4 g divinyl benzene. The iron oxide particles are added to the monomer/initiator mixture.

260 g water phase consisting of Methocel 1.8% and SDS 0.35% is prepared in a jacketed reactor mounted with an anchor stirrer and a continuous $N_2$ gas flow.

The organic phase is added to the reactor and the stirrer speed is increased to 500-600 rpm. After 30 minutes the circulation flow in the reactor of 70° C. water is started and the polymerisation reaction is left to proceed over night.

The product particles are washed by repeated centrifugation in water and ethanol.

Improving Centered Distribution of Iron Oxide in the Particles 1.25 g AMBN is dissolved in 62.4 g divinyl benzene. 16 g iron oxide particles and 0.16 g n-octadecyl phosphonic acid or 0.8 ml dimethyl dichlorosilane 2% are added to the monomer/initiator mixture.

260 g water phase consisting of Methocel 1.8% and SDS 0.35% is prepared in a jacketed reactor mounted with an anchor stirrer and a continuous $N_2$ gas flow.

The organic phase is added to the reactor and the stirrer speed increased to 500-600 rpm. After 30 minutes a circulation flow of 70° C. water in the reactor was started and the polymerisation reaction was left to proceed over night.

The product particles are washed by repeated centrifugation in water and ethanol.

Preparing Improved Polymer Layer Covering the Iron Oxide Particles 16 g of iron oxide (9 nm, 20-30 nm or <5 μm) is wetted by 3-6 ml oleic acid.

1.25 g AMBN is dissolved in 1.68-2.50 g divinyl benzene and 25.2-37.90 g styrene. The treated iron oxide particles are added to the monomer/initiator mixture.

260 g water phase consisting of Methocel 1.8%, SDS 0.35% and KI 0.65% is prepared in a jacketed reactor mounted with an anchor stirrer and a continuous $N_2$ gas flow.

The organic phase is added to the reactor and the stirrer speed increased to 500-600 rpm. After 30 minutes the circulation flow of 70° C. water in the reactor is started and the polymerisation reaction was left to proceed. After 3 h of polymerisation 0-0.83 g divinyl benzene and 0-12.4 g styrene was added to the reactor. The polymerisation reaction was allowed to proceed over night.

The product particles are washed by repeated centrifugation in water and ethanol.

Hydrophilisation of the Magnetic Polymer Particles with Diethylene Glycol Monovinylether 43.5 g magnetic polymer particles, 40 ml diethylene glycol monovinylether and 0.85 g AMBN is added to a 100 ml round-bottomed reactor. The slurry is purged with $N_2$ gas for at least 30 minutes before the reactor is immersed in an oil bath of 70° C. The reaction is allowed to proceed over night under a continuous flow of $N_2$.

The hydrophilized particles are washed by repeated centrifugation with 50% ethanol in water.

B: Encapsulation of Magnetic DVB Beads in Agarose

Agarose (0.6 g) and sedimented magnetic DVB beads (3 mL) was added to water (7 mL) and the agarose was dissolved by heating to 95° C. for 30 min. The suspension was cooled to 60° C. and was added to toluene (100 ml) and Prisorine 3700 (0.67 g) in an emulsification vessel. The emulsification vessel was equipped with a 40 mm turbine stirrer. The speed of the stirrer was kept at 300 rpm and the temperature was kept at 60° C.

After 5 minutes the speed of the stirrer was increased to 700 rpm during 15 minutes, maintaining the temperature at 60° C.

Thereafter the emulsion was cooled and the beads were allowed to gel. The beads were washed with water and ethanol and enriched using a magnet. Approximately half of the agarose beads formed contained magnetic DVB beads. These agarose beads comprise at least one inner bead of magnetic DVB, preferably at least two, such as 3-5 inner beads.

According to the invention, the method used for the preparation of magnetic poly(divinyl benzene) beads is suspension polymerisation. An important step in the preparation is that the magnetic entity, such as iron oxide powder, is pre-treated with an amphiphilic agent, such as oleic acid, which will render the material more hydrophobic so as to be dispersable in the divinyl benzene phase during synthesis.

This synthesis method uses emulsification of a oil-in-water suspension. This method results in a highly magnetically active material where the magnetite ($Fe_3O_4$) particles, are encapsulated within the bead (FIG. 1). This means that the risk of leakage at acid pH is minimised, since the poly(divinyl benzene) is chemically inert at all pH commonly used in chromatography (pH 1-14). This material is suited as the basis for further coating with a hydrophilic polymer, e.g. agarose or a hydrophilic synthetic polymer, resulting in a magnetic material encapsulated in the chemically stable poly (DVB)-material and with an external hydrophilic layer (FIG. 2).

The outer agarose layer is also suited for further derivatisation with any desirable ligand that fulfils the needs for the intended application. Such applications can be protein, nucleic acid, virus or cell separation/concentration or any diagnostic application. The magnetic beads of the invention may be used for column chromatography, chromatography in fluidised beds, batch-wise procedures, protein arrays on solid phase or in solution, high throughput analysis etc. The beads according to the invention are also suitable for cell cultivating purposes.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A magnetic bead, comprising one or more inner beads of magnetic metal particles enclosed by a coating of an inert synthetic polymer, and an outer coating of a hydrophilic porous material, wherein the outer coating is made of a natural or synthetic hydrophilic polymer, and wherein the mean particle diameter is 5-1000 μm.

2. The magnetic bead of claim 1, comprising at least two inner beads.

3. The magnetic bead of claim 1, wherein the inner coating is made of crosslinked polystyrene, poly(methacrylates) or polyacrylates.

4. The magnetic bead of claim 1, wherein the outer coating is made of agarose, dextran, cellulose, poly(vinyl alcohol) or polyacrylamides.

5. The magnetic bead of claim 1, wherein an additional inner coating is provided to prevent metal leakage.

6. The magnetic bead of claim 1, wherein the outer coating is provided with ligands having affinity for selected biomolecules.

7. The magnetic bead of claim 6, wherein the ligands are selected from the group consisting of metal chelating agents, antibodies, fractions of antibodies, proteins, members of affinity pairs, aptamers, hybridisation probes, charged groups and lipophilic groups.

8. A magnetic bead, comprising one or more inner beads of magnetic metal particles enclosed by a coating of an inert synthetic polymer, and an outer coating of a hydrophilic porous material wherein the magnetic metal particles are made of $Fe_3O_4$, the inner coating is made of poly(divinylbenzene), the outer coating is made of agarose.

9. The magnetic bead of claim 8, wherein the agarose layer is provided with protein ligands.

10. The magnetic bead of claim 8, comprising at least two inner beads.

11. The magnetic bead of claim 8, wherein the mean particle diameter is 5-1000 μm.

12. The magnetic bead of claim 8, wherein an additional inner coating is provided to prevent metal leakage.

13. A method of producing magnetic metal particles, comprising:
   a) treating magnetic metal, metal oxide or alloy particles with an amphiphilic agent;
   b) adding a polymerisable monomer and a radical initiator to the treated magnetic particles;

c) emulsifying the monomer/particle mixture in an aqueous phase and polymerising the monomer by increasing the temperature to obtain polymer-coated magnetic particles;

d) adding a hydrophilic porous polymer to the polymer-coated magnetic particles;

e) emulsifying the polymer-coated magnetic particles into the hydrophilic porous polymer; and optionally f) attaching a ligand to the outer layer of the hydrophilic porous polymer, said ligand having affinity for a selected biomolecule.

14. The method of claim 13, wherein the magnetic metal oxide particles are $Fe_3O_4$, the chemically inert polymer is divinylbenzene, and the hydrophilic porous polymer is agarose.

* * * * *